US012564702B2

(12) United States Patent
Worthley et al.

(10) Patent No.: US 12,564,702 B2
(45) Date of Patent: *Mar. 3, 2026

(54) ADJUSTABLE SHEATH DEVICE

(71) Applicant: Three Peaks Medical Pty Ltd, Norwood (AU)

(72) Inventors: Stephen Worthley, Tamarama (AU); James Nicholson, Belair (AU); Simon Belcher, Panorama (AU)

(73) Assignee: Three Peaks Medical Pty Ltd, Norwood (AU)

( * ) Notice: Subject to any disclaimer, the term of this patent is extended or adjusted under 35 U.S.C. 154(b) by 925 days.

This patent is subject to a terminal disclaimer.

(21) Appl. No.: 17/567,663

(22) Filed: Jan. 3, 2022

(65) Prior Publication Data

US 2022/0265961 A1 Aug. 25, 2022

Related U.S. Application Data

(63) Continuation of application No. 17/278,065, filed as application No. PCT/AU2019/051010 on Sep. 20, 2019, now Pat. No. 11,344,698.

(30) Foreign Application Priority Data

Sep. 20, 2018 (AU) ................................ 2018903540

(51) Int. Cl.
*A61M 25/00* (2006.01)
*A61M 25/01* (2006.01)

(52) U.S. Cl.
CPC .... *A61M 25/0023* (2013.01); *A61M 25/0009* (2013.01); *A61M 25/0045* (2013.01);
(Continued)

(58) Field of Classification Search
CPC .......... A61M 25/0023; A61M 25/0009; A61M 25/0045; A61M 25/0108;
(Continued)

(56) References Cited

U.S. PATENT DOCUMENTS

| 4,921,479 A | 5/1990 | Grayzel |
| 5,201,756 A | 4/1993 | Horzewski et al. |

(Continued)

FOREIGN PATENT DOCUMENTS

| CN | 104602718 A | 5/2015 |
| CN | 107405474 A | 11/2017 |

(Continued)

OTHER PUBLICATIONS

International Search Report and Written Opinion for International Patent Application No. PCT/AU2019/051010, dated Nov. 14, 2019 (11 pages).

(Continued)

*Primary Examiner* — Chelsea E Stinson
*Assistant Examiner* — Nelson Louis Alvarado, Jr.
(74) *Attorney, Agent, or Firm* — Goodwin Procter LLP

(57) ABSTRACT

The disclosure generally relates to adjustable sheath devices for insertion into the body to provide intravascular access to various medical devices, involving a dynamically expandable sheath capable of expanding within the blood vessel when a medical device is passed through the sheath and retracting back to almost its original size when the medical device is removed from the sheath. Embodiments generally comprise a rigid collar and an elongated sleeve comprising a continuous elastomeric outer layer and an expandable inner layer.

19 Claims, 8 Drawing Sheets

(52) U.S. Cl.
    CPC . *A61M 25/0108* (2013.01); *A61M 2025/0024*
        (2013.01); *A61M 2025/0047* (2013.01); *A61M*
        *2205/0216* (2013.01)

(58) Field of Classification Search
    CPC .. A61M 2025/0024; A61M 2025/0047; A61M
        2205/0216; A61M 2025/0681; A61M
        25/0014; A61M 2025/0046; A61M
        2039/062; A61M 25/0662; A61M 39/06;
        A61M 25/0013; A61M 25/0102; A61M
        2025/0188; A61B 2090/3966
    See application file for complete search history.

(56)                 References Cited

U.S. PATENT DOCUMENTS

| | | | |
|---|---|---|---|
| 5,318,588 | A | 6/1994 | Horzewski |
| 6,228,068 | B1 | 5/2001 | Yoon |
| 6,616,678 | B2 | 9/2003 | Nishtala |
| 7,678,128 | B2 | 3/2010 | Boyle et al. |
| 7,766,820 | B2 | 8/2010 | Core |
| 7,963,952 | B2 * | 6/2011 | Wright, Jr. ......... A61B 17/3415 |
| | | | 604/524 |
| 8,363,604 | B2 | 1/2013 | Gurelli et al. |
| 8,790,387 | B2 | 7/2014 | Nguyen et al. |
| 10,639,152 | B2 | 5/2020 | Le et al. |
| 2001/0012950 | A1 | 8/2001 | Nishtala et al. |
| 2003/0233115 | A1 | 12/2003 | Eversull et al. |
| 2010/0324490 | A1 * | 12/2010 | Pini .................. A61M 25/0668 |
| | | | 604/167.03 |
| 2011/0282156 | A1 * | 11/2011 | Lenker .............. A61B 17/3439 |
| | | | 600/208 |
| 2014/0012281 | A1 * | 1/2014 | Wang ................ A61M 25/0023 |
| | | | 606/108 |
| 2014/0142509 | A1 | 5/2014 | Bonutti |
| 2014/0236088 | A1 | 8/2014 | Al-Rashdan et al. |
| 2016/0074067 | A1 | 3/2016 | Furnish |
| 2016/0128723 | A1 | 5/2016 | Ginn et al. |
| 2017/0014157 | A1 | 1/2017 | Coyle |
| 2018/0043133 | A1 | 2/2018 | Wong |
| 2018/0161064 | A1 | 6/2018 | Fitterer et al. |
| 2018/0207395 | A1 | 7/2018 | Bulman |

FOREIGN PATENT DOCUMENTS

| | | |
|---|---|---|
| EP | 3280479 B1 | 3/2020 |
| JP | 2008512200 A | 4/2008 |
| JP | 2018510727 A | 4/2018 |
| JP | 2022508478 A | 1/2022 |
| WO | WO-2014/081810 A2 | 5/2014 |
| WO | WO-2015/063497 A1 | 5/2015 |
| WO | 2016164079 A1 | 10/2016 |
| WO | WO-2016164082 A1 | 10/2016 |
| WO | WO-2018213222 A1 | 11/2018 |

OTHER PUBLICATIONS

Communication of a Notice of Opposition for European Patent
Application No. 19862400.9 dated Jul. 24, 2024 (45 pages).
Summons to Attend Oral Proceedings for European Patent Appli-
cation No. 19862400.9 dated May 30, 2025 (13 pages).

* cited by examiner

210

200

230

220

240

ADJUSTABLE SHEATH DEVICE

TECHNICAL FIELD

The technical field generally relates to adjustable sheath devices for insertion into the body to provide intravascular access to various medical devices. This includes but is not limited to all arterial and vasculature access, abdominal and thoracic cavities, cerebrospinal, genito-urinary and gynaeco-logical, upper gastrointestinal and colorectal procedures. Embodiments generally provide a dynamically expandable sheath capable of expanding within the blood vessel when a medical device is passed through the sheath and also capable of retracting back to almost its original size when the medical device is removed from the sheath.

BACKGROUND

Vascular introducer sheaths are common to intravascular procedures, such as transcatheter aortic valve replacement (TAVR), angioplasty and stenting, to facilitate access to the vascular system for the introduction of removable devices such as wires, balloons, pressure transducers and for the introduction and placement of implantable devices such as mechanical aortic valves and stents.

Vascular introducer sheaths typically consist of a single hollow radial cuff or sleeve through which a device may be passed once the introducer sheath is inserted, manoeuvred and placed within the patient's vasculature. The sleeve terminates at one end with a radial collar which is positioned on the patient's skin and within an opening to a blood vessel. The collar typically creates a temporary seal around the opening to the vessel and may include one or more inlets to allow devices and fluids to be passed into the patient's vascular system through the sleeve cavity.

Vascular introducer sheaths are also designed to protect the blood vessel from physical damage that can arise from the insertion of a medical device into the vasculature, particularly where devices are large with respect to the luminal cavity of the vessel. For example, TAVR procedures are typically conducted through the femoral artery, which, in older patients is often smaller in diameter that the device itself. This frequently leads to damage of the artery from the shear forces between the artery wall and the device.

It is common practice during intravascular procedures to insert and remove a series of introducer sheaths of increasing diameter to widen the vascular opening or the vessel until it is large enough to allow for the safe and unobstructed passage of the intravascular device. Depending on the size of the patient's vasculature, procedures commence with the introduction of introducer sheaths of a small diameter and progressively increase in diameter until the aperture and introducer sheath are large enough to allow for the delivery of the removable or implantable device.

For instance, the introduction and delivery of a transcath-eter aortic valve typically involves the insertion of a smaller calibre introducer to dilate the arterial access site and vasculature, prior to the insertion of the definite sized sheath and introducer which are often between 14 and 20 French in calibre, depending upon the size required to deliver the transcatheter aortic valve replacement system.

The insertion and removal of each introducer sheath adds to the overall procedure time and increases risk of damage to the vessel wall. While attempts are made to maintain sterility of apparatus and to follow aseptic procedures within theatre rooms, the mere presence of an intravascular opening and introduction of foreign objects into the patient intro-duces a risk of infection, which increases as the number of objects and duration of the procedure increases. In addition, blood loss and stress to the patient increases with procedure time and with the introduction of objects into the patient. Vascular injury from abrasion of the luminal surface of the vessel or even rupturing of the vessel itself is a significant risk at the opening of the vessel; as the introducer sheath is inserted into the patient and within the patient's vessels, once the introducer sheath is navigated through the patient's vascular system.

Previous attempts to design and develop expanding intro-ducer sheaths that minimise the need to introduce multiple sheaths during intravascular procedures have been largely unsuccessful. Expanding sheaths are designed to be inserted when retracted at a small diameter, enlarged once placed within the vessel and retracted again to reduce their diameter prior to removal. However, many are developed from bonded composite materials with an expanding portion running longitudinally on the sheath. These devices are minimally expanding as only a section of the composite sheath material is capable of expanding and frequently do not expand sufficiently to alleviate the need to introduce a second or third larger introducer sheath into the patient. The engineering of such composite structures frequently results in device failure as the expanding section introduces a weakening in the structure which collapses when forced through the vascular system; resulting in the 'ridging' or buckling of the introducer sheath within the vessel. Further, expanding sheaths typically fail to retract to their original diameter frequently causing injury to the vessel or the opening of the vessel during their removal.

When placed within that patient via an opening in the femoral artery, for instance, the introducer sheath plays an essential role in protecting the patient's peripheral vascula-ture from injury or trauma that may otherwise arise from the passage of an introducer or device through sections of curved or complex vascular channels. However, due to the likelihood of failure of many introducer sheaths, which are too rigid to navigate these curved and complex sections of vasculature and consequently kink and buckle during inser-tion and placement, sheathless techniques are still frequently practiced during many surgeries. Physicians must make a trade-off between the safety of the sheath when passing through complex areas such as the ilio-femoral system, and the unsheathed device; as the devices themselves are prone to catch or tear at the luminal surface at curvatures in vessels.

For procedures such as TAVR, which present a viable alternative to more invasive and risky open heart surgeries, the safe passage of guidewires, introducers and the mechani-cal valve itself through the peripheral vascular system are essential to broadening the accessibility of these vital cor-rective surgeries to cohorts of patients that would otherwise fail to qualify for them.

For many cohorts of patients, such as the elderly, tradi-tional heart surgeries to correct functional defects in aortic valves are simply too risky. TAVR presents a safer alterna-tive for these patients. However, TAVR procedures per-formed with current medical technologies and best practices on average in Australia still result in 5.5% of patients suffering major vascular complication, 8.5% with major bleeding, 1.6% with stroke and 1.6% with myocardial infarction. Potential causes of these vascular injuries in TAVR include the patient's vascular calibre, the presence of atherosclerosis, the calibre of the introduced and withdrawn sheath, characteristics of the sheath including its rigidity and the degree to which it is prone to kink or ridge.

Therefore, it is anticipated that addressing any one of these areas of vascular injury during TAVR will improve the safety of TAVR procedures and will open the procedure up to an even greater cohort of patients that are currently unable to access aortic replacement surgery.

SUMMARY

In various aspects, the embodiments of the present invention relate to a retractable sheath for protecting the luminal surface of a blood vessel from the introduction of a medical device within the blood vessel, the retractable sheath comprising; a rigid collar having an inner surface defining an opening extending through the collar, the rigid collar having attached thereto a circumferentially retractable elongated sleeve having a proximal opening and a distal opening defining a luminal channel therebetween, the elongated sleeve comprising two separate layers including a continuous elastomeric outer layer and an expandable inner layer discontinuous at least in part, the discontinuous part of the expandable inner layer comprising a stiff polymeric sheet characterised as having outward annular resistance when forcibly coiled, the stiff polymeric sheet forming at least part of the expandable inner layer when coiled and positioned longitudinally within a lumen formed by the continuous elastomeric outer layer and positioned substantially in contact with a luminal surface of the continuous elastomeric outer layer, wherein the rigid collar is attached to the circumferentially retractable elongated sleeve the proximal opening of the sleeve.

Embodiments designed as such provide a dynamically expandable sheath capable of expanding within the blood vessel when a medical device is passed through the sheath and are also capable of retracting back to almost their original size when the medical device is removed from the sheath.

This functionality is achieved from a unique design concept, whereby the elastomeric outer layer provides resistive pressure to expansion of the elongated sleeve to force the retraction of the sleeve, and the expandable inner layer provides a small amount of resistive pressure to the retraction of the sleeve to form a channel within it, however the resistive pressure of the elastomeric outer sleeve is greater than the resistive pressure of the expandable inner layer. This configuration results in the passive retraction of the sleeve as a medical device is passed through the sleeve. This design contrasts significantly with traditional introducer sheaths which have a retracting outer or a single expanding and retracting layer, which generally fails to retract evenly in a radial fashion, thereby causing ridging of the sheath, or failure to retract closely enough to its original size to enable the safe removal of the sheath.

It is well understood that introducer sheaths must offer a balance of characteristics including sufficient bendability to navigate a network of vascular channels, sufficient rigidity to prevent kinking and buckling, and sufficient resilience to retract when circumferentially expanded, or when inadvertently bent or kinked. The design concept enables a complementarity of physical characteristics to be provided. Each layer of the elongated sleeve imparts different physical characteristics to provide a complementarity of physical properties that cannot be provided by any single material. In particular, the expandable inner layer of embodiments provides rigidity while the elastomeric outer layer provides resilience and both provide a sufficient degree of bendability to navigate a patient's vasculature.

Furthermore, the orientation of the seam along length of the expandable inner layer and/or the degree of lapping of the expandable inner layer can also be altered to adjust and optimise the resilience and flexibility of the sheath.

Additionally, the multi-layer design concept according to embodiments may provide a better opportunity for persons skilled in the art to optimise physical properties of the retractable sheath by allowing for a broader selection of materials for forming the elastomeric outer layer and the expandable inner layer, or it may offer the opportunity for persons skilled in the art to localise desired physical properties of the retractable sheath.

Selection of suitable materials must also be suited to the desired shape of the expandable sheath or the elongated sleeve. Particular shapes may impart functional characteristics that may be desired in certain embodiments.

For instance, to ease insertion, embodiments may comprise an elongated sleeve that is longitudinally tapered at least partially between the proximal opening and the distal opening. The degree of tapering may be critical for certain uses, for instance, for TAVR procedures where the valve may well be larger than the patient's femoral artery, the degree of tapering preferably facilitates ease of entry of the retractable sheath into an opening in the vessel where the opening of the vessel and the vessel itself may be gently stretched and enlarged by insertion of the tapered sleeve and access of the device may be eased by insertion into the larger opening of the sleeve. Further, tapering may permit expansion of the sheath with less introducing force than a non-tapered expanding sheath.

Therefore, the sleeve edge defining the distal opening preferably has a circumference about at least about 20% smaller than the sleeve edge defining the circumference of the proximal opening. Or, more specifically, the sleeve edge defining the distal opening preferably has a circumference at least about 25% smaller than the sleeve edge defining the circumference of the proximal opening. For many indications such as TAVR, a distal opening having a circumference of at least about 35% of the circumference of the proximal opening is preferred. In practice, a preferred circumference of the distal opening is in a range of between about 35% and 40% of the circumference of the proximal opening.

Shapes such as tapering, may be achieved by shaping just one of the elastomeric outer layer or the expandable inner layer. For instance, the expandable inner layer may be shaped to be cylindrical with no taper, and the taper of the elongated sleeve imparted by a tapered elastomeric outer layer. Further, the tapered shape of the expandable inner layer may be achieved by a coiling the stiff polymeric sheet into a tapered shape.

The design of retractable sheaths of certain embodiments may comprise an elongated sleeve comprising a substantially cylindrical portion terminating at the proximal opening. In particular, the expandable inner layer may comprise a substantially cylindrical continuous portion terminating at the proximal opening and a discontinuous stiff polymeric sheet portion terminating at the distal opening coiled and positioned longitudinally within the lumen formed by the continuous elastomeric outer layer and positioned substantially in contact with the luminal surface of the continuous elastomeric outer layer.

In preferred embodiments, the substantially cylindrical portion terminating at the proximal opening is sized to promote a robust seal to the vascular opening. This non-tapered portion of the expandable inner layer may comprise an axial seam or joint line and may be integrally formed with the discontinuous tapered portion. Preferably, the overlap of the discontinuous tapered portion of the coiled stiff polymeric sheet increases from the proximal end to the distal end, creating a helical edge along the length of the elongated sleeve. An angled edge may aid the smooth expansion and retraction of the expandable inner layer.

Further, the number of turns of the helically wound stiff polymeric sheet alters its properties through resistance to radial expansion and contraction, as well as bendability of the sheath as the longitudinal stiffness of the stiff polymeric sheet is broken or relaxed along the length of the sheath.

The expandable inner layer may comprise cut outs, slits and other sections to improve or alter the physical properties of the elongated sleeve, in particular, the bendability, resistance to kinking or resilience of the elongated sleeve.

The expandable inner layer may be integrally formed from a substantially uniform stiff polymeric material comprising a notch or cut-out between the substantially cylindrical continuous portion and the discontinuous stiff polymeric sheet portion. The discontinuous stiff polymeric sheet portion may be configured to coil in an overlapping arrangement in its relaxed state and to coil helically about the longitudinal axis of the elongated sleeve.

Helical winding is preferred as it typically facilitates the expanding and retracting of the discontinuous stiff polymeric sheet portion. It also has the best combination of properties of reduced kinkability and most typically flexibility during introduction.

In particular, an edge of the discontinuous stiff polymeric sheet portion may wind helically about the longitudinal axis of the elongated sleeve. The discontinuous sheet portion preferably winds about the longitudinal axis of the sheath a number of times approximately equal to the number of times the distal portion is wound plus about 0.5 to about 1.5. More particularly, the number is approximately equal to the number of times the distal portion is wound plus about 1.

The number of turns of the discontinuous stiff polymeric sheet portion about the longitudinal axis of the elongated sleeve and the degree of overlap of the discontinuous stiff polymeric sheet portion upon itself as it winds helically about the longitudinal axis of the elongated sleeve may both, individually or together, alter the performance properties of the sheath. Axial stiffness along the length of the sheath increases as the degree of overlapping of the discontinuous stiff polymeric sheet portion increases, however, stiffness may be decreased with an increase in the number of turns of the discontinuous stiff polymeric sheet portion upon itself about the longitudinal axis of the elongated sleeve.

Winding of the discontinuous stiff polymeric sheet portion about the longitudinal axis of the sheath may be increased up to a number of times approximately equal to the number of times the distal portion is wound plus about 2. This may adjust the annular resistance of the sheet for the passage of a medical device through it, which in turn may assist in protecting the luminal wall of the patient's vasculature. Conversely, winding may be decreased down to a number of times approximately equal to the number of times the distal portion is wound plus about 0.5 to adjust the flexibility of the sheath by reducing the degree of overlapping of the stiff polymeric sheet and breaking the degree of longitudinal stiffness of the stiff polymeric sheet.

The shape of the notch or cut out can be selected from a variety of shapes, for example circular, triangular, ovoid, or T-shaped and may be selected on the basis of the desired physical properties of the elongated sleeve.

The expandable inner layer may comprise a series of small cut outs along its length which may improve the bendability of the elongated sleeve. For instance, this may include a series of notches or a series of slits.

In an alternative embodiment the expandable inner layer may be configured from a continuous thin strip. The strip may further comprise a series of longitudinal coils projecting from an edge, wherein the coils wind back over the continuous thin strip. The wound coils are typically of length between 1 mm and 10 mm, with a spacing between them of 0.1 mm to 10 mm. In certain embodiments, the diameter of each coil may be consistent along the length of the continuous strip, or be of varying diameter along the length whereby at least the coil at the distal end is a smaller diameter to the coil at the proximal end.

The stiff polymeric sheet of embodiments may be formed from a material comprising at least one member selected from the group consisting of polyethylene, polypropylene, nylon, polyester, PTFE, co-polymers thereof or other biologically compatible polymers. Preferably the stiff polymeric sheet is formed from polypropylene.

Where certain materials are adopted, the discontinuous portion of the expandable inner layer may be prone to becoming locked in an expanded position as the edges of the overlapping portions may abut against one another and become locked in that position. To avoid this problem such edges may be rounded, blunt, or cut at a non-orthogonal angle.

The design of the stiff polymeric sheet may comprise at least three edges, wherein at least one edge terminates in an oblique cut. Further, at least two substantially opposite edges may intersect at a point or edge defining the distal opening and the at least one of the two edges are formed by an oblique cut.

In an alternative embodiment, the expandable inner layer may be formed from a helically wound continuous strip or wire. It may be characterised by a strip or wire thickness of dimension 'W', wherein it is wound with a helical pitch of between 'W' and '2W'.

Preferably, the pitch of the helical strips is between about 0.5 lengths to 2 lengths where each length is the axial length of the split. More specifically, a preferred helical pitch is 0.9 lengths to 1.1 lengths.

The helical wire may be constructed of titanium, titanium alloy or stainless steel, or of a polymeric material such as polyester, polyethylene, polypropylene or other biocompatible material. It may be tapered along the length of the elongated sleeve.

The prior art describes multi-layer sheaths in which two or more layers are bonded to one another. An inherent feature of the design concept of embodiments is that the combination of the physical characteristics of each layer is lost when layers are bonded together.

Thus, in preferred embodiments, the continuous elastomeric outer layer and the expandable inner layer are movable with respect to one another. Preferably, the luminal surface of the continuous elastomeric outer layer and an outer surface of the expandable inner layer are movable with respect to one another, and preferably have a low coefficient of friction. Acceptable coefficients of friction are well known to persons skilled in the art, thus the selection of materials that have an inherent coefficient of friction that is adequately low is well known to such persons.

Regardless however, the inner and outer layers may be fixed relative to each other at the proximal end, which may be through direct relative attachment through welding, bonding or clamping, or which may be achieved through attachment of both tubes to a haemostatic valve or similar device. This ensures that the layers, while they are enabled to move relative to one another, remain fixed in a desired position.

In particular, the proximal end of the inner layer may be attached to the rigid collar by bonding an area of the exterior surface of the expandable inner layer to the inner surface of the rigid collar. The elastomeric outer layer may be maintained in place once positioned upon the exterior surface of the rigid collar by virtue of a relaxed proximal circumference equal to or less than the outer circumference of the rigid collar.

In certain embodiments, the elongated sleeve may comprise a lubricious layer or surface treatment between the luminal surface of the continuous elastomeric outer layer and the outer surface of the expandable inner layer. Preferably, these comprise at least one member selected from the group consisting of silicon, glycerine oil, PTFE, or a hydrophilic polymer to reduce the coefficient of friction. The lubricious layer may further comprise hydrogel-based coatings that can include medicinal agents to treat or avoid infections or allergies. These substances or other hydrophilic coatings may be applied to the inner surface of the expandable inner layer to reduce the coefficient of friction between the medical device and the retractable sheath.

Turning now to the design of the elongated sleeve of several embodiments, the continuous elastomeric outer layer may be comprised of an elastomeric material, such that the continuous elastomeric outer layer is capable of being expanded upon stretching of the elastomeric material and retracted upon relaxation of the elastomeric material. Preferably, the selection of suitable materials enables the elastomeric material to be capable of returning to a circumference of about 135% or less of its initial circumference once retracted. Typically, the resting circumference of the proximal edge will be about 135% greater than the resting circumference of the distal edge, thus, the elastomeric material must be capable of returning to a circumference of at least the size of the proximal opening. More preferably, the elastomeric material to be capable of returning to a circumference in the range of about 115% and about 120% of its initial circumference once retracted. This may however be about 117%.

Further, the selection of suitable materials may enable the continuous elastomeric outer layer must be capable of being expanded upon stretching of the elastomeric material to about 1.35 times or greater of its unstretched circumference. The desirable capacity of the elastomeric to expand would ideally not limit the types of medical devices that may be passed through it, therefore the continuous elastomeric outer layer is preferably capable of being expanded upon stretching of the elastomeric material to between about 300% to 400% of its unstretched circumference.

Preferably, the continuous elastomeric outer layer is formed from a member of the group consisting of latex rubber or non-latex substitutes including nitrile rubber, polyvinylchloride, neoprene, polypropylene and polyisoprene. Preferably the continuous elastomeric outer layer is formed from a silicone material or a silicone composite material.

Preferred materials for forming the elastomeric outer layer are selected from those that may be formed to a thinness, without rupturing, having a sufficient resistant pressure to retract the expandable inner layer. In doing so, the user need not apply significant force to the medical device during insertion to forcibly expand the elastomeric outer layer, which may otherwise risk damage to the vessel. Thus, the continuous elastomeric outer layer preferably comprises a thickness of about 0.2 mm or less. Or more specifically, the continuous elastomeric outer layer preferably comprises a thickness of about 0.1 mm.

In preferred embodiments, the rigid collar is provided by a haemostatic valve connector. The haemostatic valve connector may comprise a haemostatic valve to prevent the patient losing blood from the opening in the vessel. The haemostatic valve connector may further comprise a opening for introducing a medical device into the lumen of the elongated sheath. It may also comprise one or more inlets for introducing fluids into the patient's vascular system.

To promote visibility of a medical device or the retractable sheath to x-ray imaging equipment during medical procedures, the elongated sleeve may comprise a radio opaque marker. The radio opaque marker is preferably located at the distal end of the elongated sleeve and may equally be bound to the elastomeric outer layer or the expandable inner layer. The marker may be a metallic wire such as nitinol, bonded or stitched to the sleeve, or it may be polymer-based such as a tungsten-filled nylon, polyethylene or polyurethane, bonded to the sleeve. Alternatively, the radio opaque marker may be bonded to the elastomeric outer layer and the expandable inner layer, thus binding the layers together at the distal end of the elongated sleeve.

During the insertion of the retractable sheath into the patient a rigid introducer may be inserted within the expandable inner layer. In certain embodiments, the retractable sheath may be provided with a rigid introducer within the lumen of the elongated sleeve and protruding past the distal end of the elongated sleeve.

Upon insertion, the rigid introducer may protrude past the distal end of the expandable inner layer. The rigid introducer typically has a tapered tip. It may include a small hole to allow passage of a wire that may have been previously inserted into the vessel.

The rigid introducer may be tapered to align with the diameter of the distal opening in the elongated sleeve or to align with the outer profile of the elongated sleeve.

Alternatively, the external surface of the rigid introducer may be stepped to match both the distal inner diameter of the expandable inner layer and proximal inner diameter of the expandable inner layer.

Following insertion of the retractable sheath, the rigid introducer may be removed to allow other devices to be routed through the lumen of the elongated sleeve.

The use of a retractable sheath according to embodiments may therefore comprise the steps of; obtaining a retractable sheath according to embodiments, passing a rigid introducer through the lumen of the retractable sheath, and introducing the retractable sheath into a blood vessel.

A method according to embodiments may comprise the additional steps of removing the rigid introducer, and passing a medical device through the lumen of the retractable sheath.

A retractable sheath according to embodiments is preferably manufactured by obtaining a rigid collar, an elastomeric outer layer and an expandable inner layer as described in accordance with embodiments, attaching the expandable inner layer at the proximal opening with the rigid collar, and placing the expandable inner layer within the elastomeric outer layer.

Alternatively, the elastomeric outer layer may be co-moulded within the rigid collar.

Broad embodiments of the invention now will be described with reference to the accompanying drawings together with the Examples and the preferred embodiments disclosed in the detailed description. The invention may be embodied in many different forms and should not be construed as limited to the embodiments described herein. These embodiments are provided by way of illustration only such that this disclosure will be thorough, complete and will convey the full scope and breadth of the invention.

DESCRIPTION

Brief Description of the Figures

FIG. 4(a) provides a side view of an adjustable sheath according to embodiments, wherein

FIG. 6 provides a front perspective view of an adjustable sheath according to embodiments with the outer elastomeric tube removed, wherein

Several embodiments of the invention are described in the following examples.

DETAILED DESCRIPTION OF EMBODIMENTS

Figure 1:
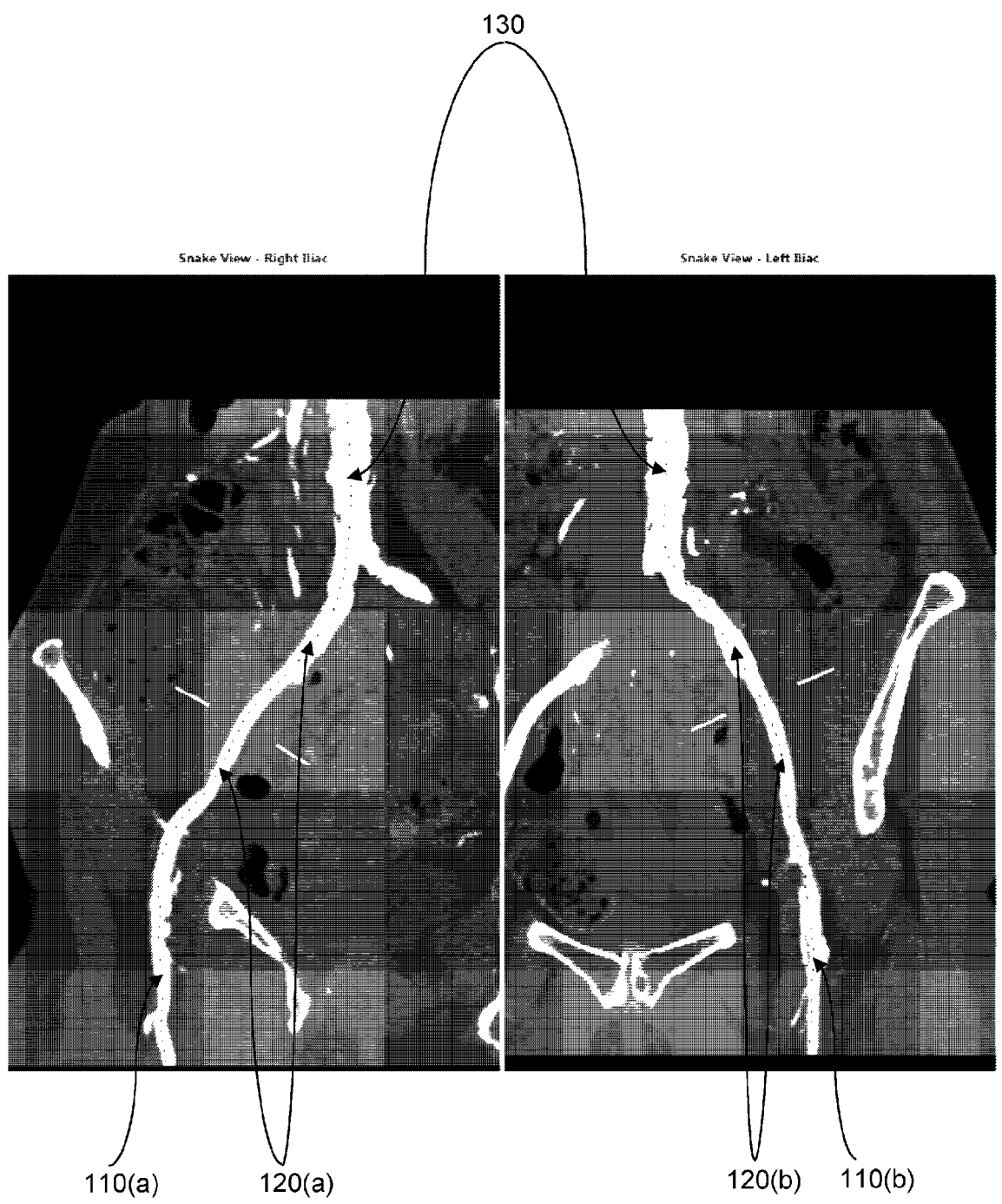
FIG. 1 provides a Computed Tomography scan showing the channel of passage from the femoral arteries, through of the right and left iliac arteries to the abdominal artery.

The Computed Tomography scan illustrated at FIG. 1 shows the channel of passage that a removable or implantable medical device, such as a mechanical aortic valve, must take when being delivered through an trans-arterial route from the femoral arteries, through the right and left iliac arteries to the abdominal artery. The termini of the right and left femoral arteries are shown at 110(a) and 110(b), respectively. The right and left iliac arteries are shown at 120(a) and 120(b), respectively, and the abdominal artery is shown at 130. The path of passage of a medical device inserted at the femoral artery to the abdominal artery is shown along the dotted line, in the left image for entry via the right femoral artery 120(a) and in the left image for entry via the left femoral artery 120(b) in the right image.

The shape of the channel of passage shown in FIG. 1 illustrates some of the vascular curvatures that must be traversed by medical devices during insertion to arrive at the location required for placement. As the images are only two dimensional, they do not illustrate the path that must be navigated in the third dimension around complex bone structures including the pelvis. In use, the device is typically attached to an elongated introducer to pass and manoeuvre the device through the vascular system, often, significant force is placed upon the introducer to force the device through the vascular lumen. During this process the greatest risk of vascular damage occurs where the vessel is at its narrowest. Introducer sheaths, of the type described herein, protect the luminal surface from damage arising from the insertion of medical devices and/or introducers. Depending on the nature of the device or location of insertion or delivery, an introducer sheath may be a short structure for placement and protection around the opening of the vessel and a short way into the vessel, or it may be elongated to extend a longer way from the opening of the vessel to protect a longer section of the luminal wall.

Figure 2:
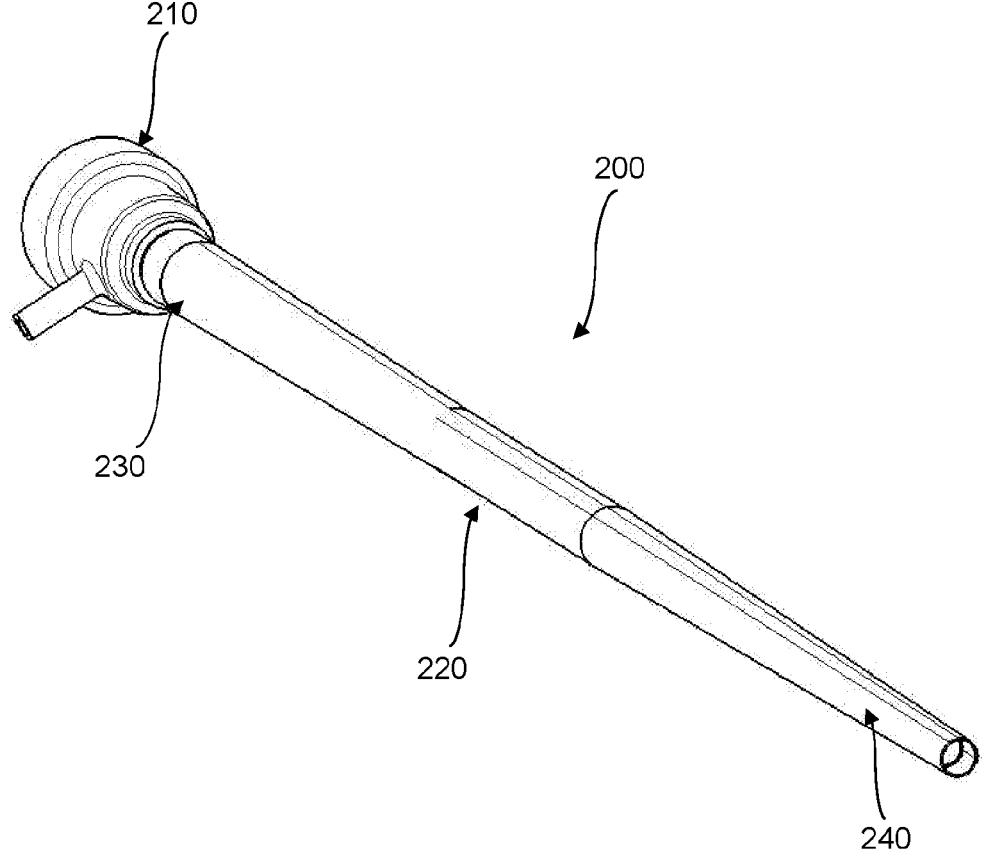
FIG. 2 provides a front perspective view of an adjustable sheath according to embodiments of the invention.

FIG. 2 illustrates an adjustable sheath 200 suitable for use as an introducer sheath as described above. Adjustable sheath 200 is broadly constructed of two main components; a rigid cylindrical collar 210 and an elongated, tapered sleeve 220. Collar 210 is a hollow structure constructed to allow materials to be fed into the inner lumen of sleeve 220 through the wider opening of the sleeve. Cylindrical collar 210 is formed of a rigid material to allow a user to handle the collar and pass an object or material therethrough. It terminates in a narrowed opening of a similar diameter to the wider opening of sleeve 220 to enable sleeve 220 to be placed and secured therein, thereby connecting the two components.

Sleeve 220 tapers away from collar 210 for ease of insertion within an incision made to access the patient's vascular system. Sleeve 220 is a smooth, flexible structure tapering from proximal end 230 and narrowing towards distal end 240 to ease the insertion and navigation of the sheath within a vessel. Sleeve 220 is expandable and retractable to enable a wider introducer, valve or other medical device to be introduced into the patient through the lumen of the sleeve, which is capable of expanding around the device, and gently press against the luminal wall of the vessel as it travels through the vessel; and then to also retract to a size similar to its original size once the device is removed, so that it can be gently removed from the patient.

Figure 3A:
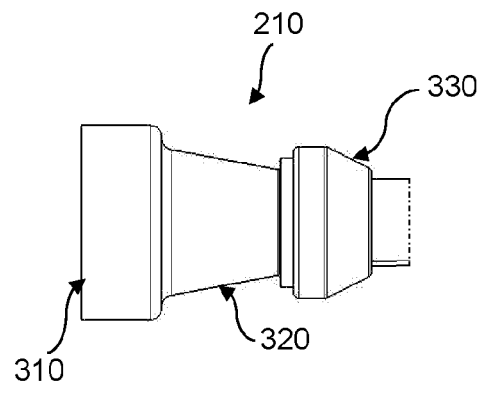
FIG. 3 illustrates a sheath collar according to embodiments wherein FIG. 3(a) provides a side view, FIG. 3(b) provides a rear perspective view, and FIG. 3(c) provides a front perspective view.
Figure 3B:
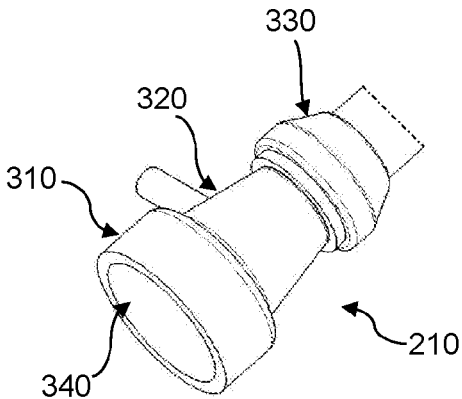
Figure 3C:
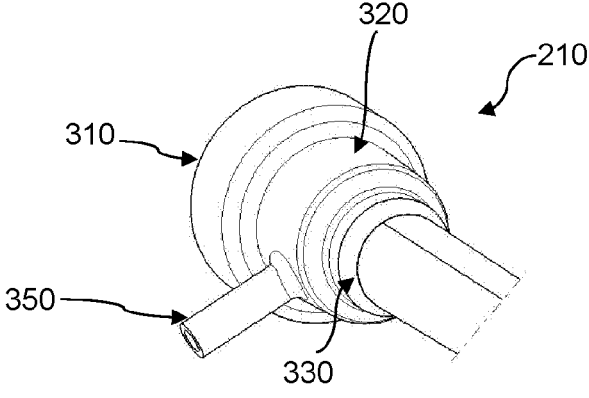

FIG. 3 illustrates the structure of sheath collar 210. FIG. 3(a) illustrates three main sections formed within collar 210 including a valve portion 310 having a haemostatic valve therein (not shown), a connector portion 320 for providing inlets or other connectors for access to the vessel, and a securement portion 330 for securing the sleeve 220 (not shown) therein. FIG. 3(b) shows the location of haemostatic valve 340 positioned within valve portion 310. Haemostatic valve 340 may be pierced or penetrated to allow the entry of devices through the sheath collar and into the lumen of the sleeve, and will return to a closed position to preventing the backflow of fluids from the vessel. FIG. 3(c) shows the location of inlet 350 for the connection of medical fluid lines to the sheath collar for the introduction of fluids into the patient.

Collar 210 is formed from a rigid polymer such as polyethylene, polyester or polypropylene, however, it may equally be formed from any rigid, biocompatible material determined by those skilled in the art as being suitable for the intended purpose.

Figure 4A:
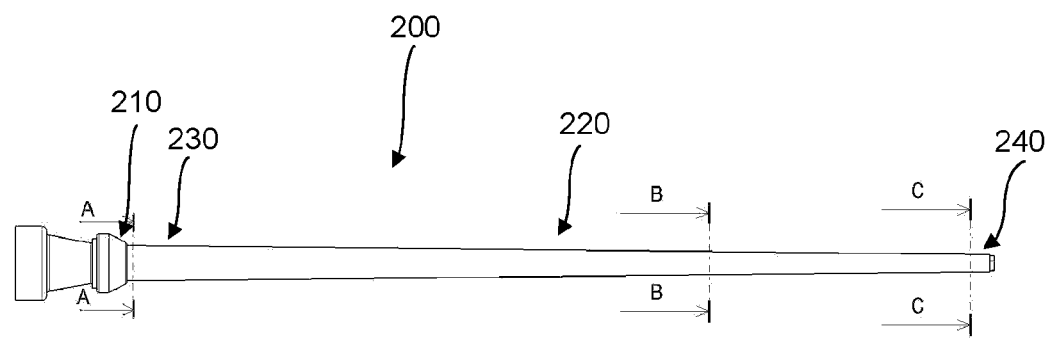

FIG. 4(a) provides a side view of expandable sheath 200, illustrating the exterior of the collar 210 and the exterior surface of the sleeve 220. Sleeve 220 is formed of two thin, flexible layers; outer elastomeric tube 410 and expanding inner layer 420. Outer elastomeric tube 410 is formed as an elongated, tapered tube maintaining within it a coiled sheet forming expanding inner layer 420.

Outer elastomeric tube 410 is formed from an elastomeric material that can be stretched when pressure is exerted from within the lumen of the sleeve but also substantially returns the sleeve to its original diameter once internal pressure is relaxed. The outer elastomeric tube, in a relaxed state, it has wall thickness of less than 0.2 mm, and preferably less than 0.1 mm. Elastomeric tube 410 is formed from silicone to maximise the elasticity and minimise wall thickness and thereby minimise the risk of damage to the vascular system. However, other materials may be selected by those skilled in the art for this use once determined as having suitable properties. These may include materials such as latex rubber or non-latex substitutes including nitrile rubber, polyvinyl-chloride, neoprene, polypropylene and polyisoprene and the like.

Figures 4B, 4C:
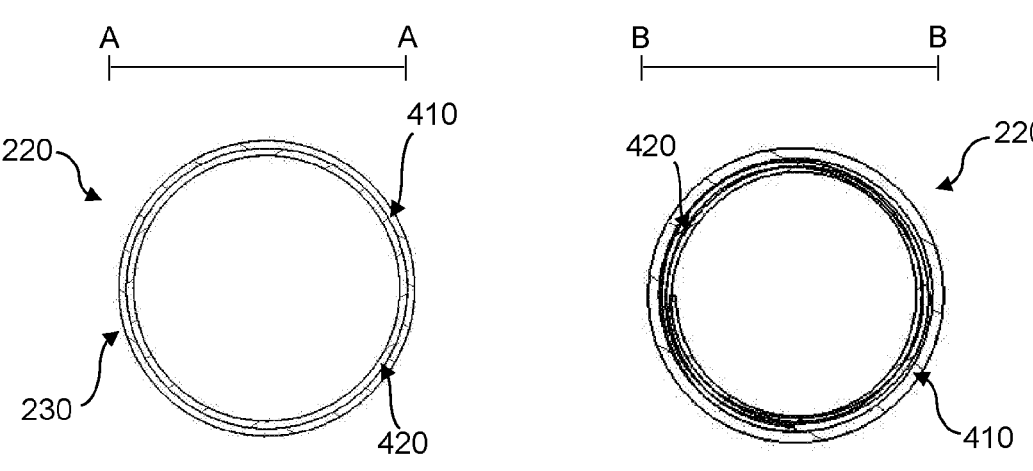
FIG. 4(b) shows a cut through view at section A-A.
FIG. 4(c) shows a cut through view at section B-B.
Figure 4D:
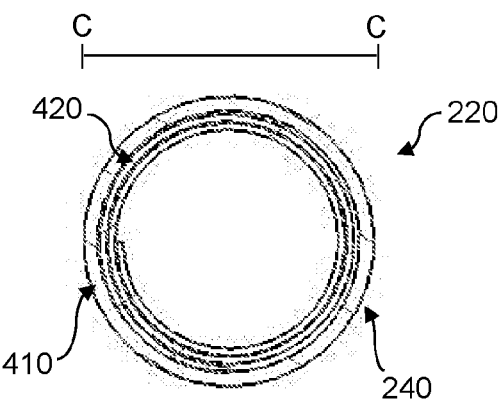
FIG. 4(d) shows a cut through view at section C-C.

FIG. 4(*a*) illustrates sectional points at points A-A, B-B and C-C. FIG. 4(*b*) illustrates a cut through section at point A-A, showing the sleeve in a relaxed state at its widest diameter, at proximal end 230, whereby the outer elastomeric tube 410 is also at its widest diameter. At section A-A, expanding inner layer 420 is uniformly a single layer thick around the entire internal circumference of sleeve 220.

FIG. 4(*c*) illustrates a cut through section at point B-B, showing the internal structure of sleeve 220 where outer elastomeric tube 410 is tapered and has a reduced diameter than at section A-A. Expanding inner layer 420 is shown to be overlapping to the extent that the inner layer is folded over twice. Whereas FIG. 4(*c*) illustrates a cut through section at point C-C, showing the internal structure of sleeve 220 where outer elastomeric tube 410 is at its narrowest, at distal end 240 of sleeve 220. At this point, expanding inner layer 420 is shown to be overlapping to the extent that the inner layer is folded over three times.

The inner tube may be made of a polymer material such as polyethylene, polypropylene, nylon, polyester, PTFE or other film-like material.

Expanding inner layer 420 is formed as a sheet of polymeric material such as polyethylene, polypropylene, nylon, polyester, PTFE or other film-like material sheet trimmed to the approximate length of outer elastomeric tube 410 to a width required to be wound three times within distal end 240 of sleeve 220. A suitable material is selected due to its stiffness when wound helically at a pitch equal to the helical pitch at the distal end plus about 1. However, as would be well known to those skilled in the art, several materials may be suitable for forming expanding inner layer 420.

While the expanding inner layer may be constructed from a sheet that is wound or coiled, more successful construction commences with an extruded tube which is subsequently sliced along its longitudinal axis and the sheet portion then wound or coiled. Suitable materials have a balance of resilience and flexibility to allow expansion and contraction without permanent deformation, and they resist buckling and collapse. Likely material choices are polypropylene or polyethylene.

Expanding inner layer 420 and outer elastomeric tube 410 are fixed relative to one another at proximal end 230. They may be attached through welding, bonding or clamping, or by attachment of each to collar 210. Along the length of sleeve 220, expanding inner layer 420 and outer elastomeric tube 420 are free to move relative to one another. A lubricant such as oil, grease, hydrogel or other low friction surface treatment may be applied between expanding inner layer

420 and outer elastomeric tube 420 to facilitate movement between them. At distal end 240 of sleeve 220, expanding inner layer 420 and outer elastomeric tube 410 may be attached to one another at a section of the circumference of outer elastomeric tube 410. They may be attached through welding, bonding or stitching.

Expanding inner layer 420 and outer elastomeric tube 410 may also be stitched or stapled together with an x-ray opaque material such as stainless steel, titanium, nickel-titanium alloy or other metal or metal alloy, for sensing.

Figure 5A:
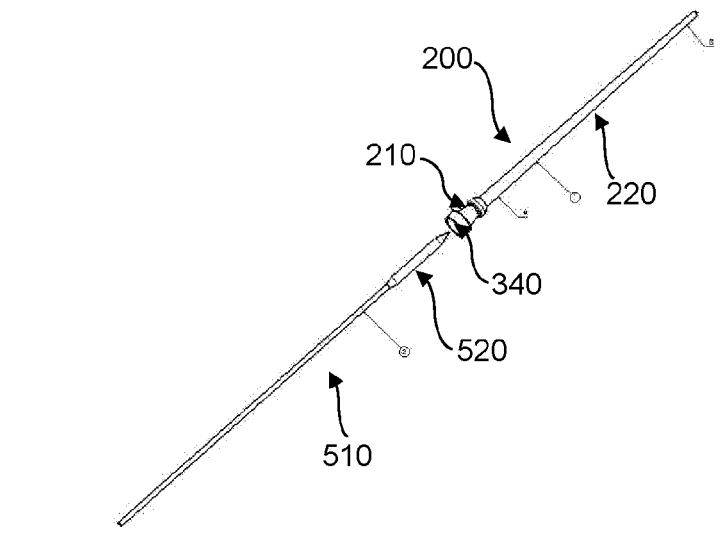
FIG. 5(a) provides a rear perspective view of an adjustable sheath according to embodiment together with an introducer, FIG. 5(b) provides a side view of the introducer passing through the adjustable sheath lumen, and FIG. 5(c) provides a section view of the adjustable sheath and introducer at section D-D.
Figure 5B:
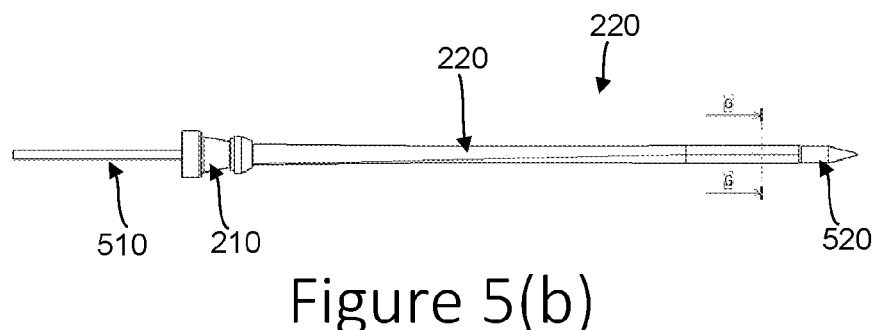
Figure 5C:
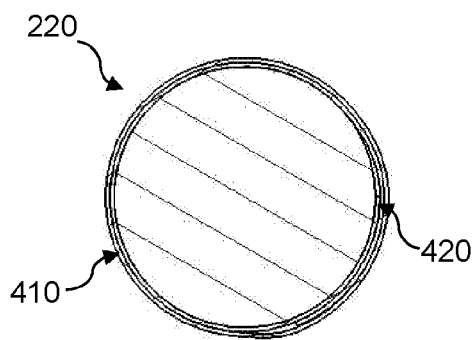

FIGS. 5(*a*) to 5(*c*) illustrate an exemplified use of adjustable sheath 200 upon passage of introducer device 510 through the inner lumen of adjustable sheath 200. During insertion into the vascular system introducer device 510 can be pushed passed haemostatic valve 340 and through the inner lumen of sheath collar 210 and inserted through expanding inner layer 420 (not shown) of sleeve 220. As shown in FIG. 5(*b*) introducer device 510 protrudes past distal end 240 of sleeve 220 through the expanding inner layer 420. Tapered tip 520 of introducer device 510 can temporarily be retained within distal end 240 of the outer elastomeric tube 410. FIG. 5(*c*) illustrates expanding inner layer 420 gradually expanding to reduce the degree to which it overlaps upon itself.

Additionally, to promote ease of feeding devices through expanding inner layer 420, the inner surface of its luminal wall may be coated in a lubricious coating such as silicone or glycerine oil, PTFE, hydrophilic polymer or other low friction surface.

In a similar fashion, outer elastomeric tube 410 can be coated externally in a low friction layer to promote ease of insertion into the vascular system. Surface treatments can include those potentially applied to the expanding inner layer, as well as hydrogel-based coatings that can include medicinal agents to treat or avoid infections or allergies.

Introducer device 510 is formed with a tapering at its tip to match the inner profile of expanding inner layer 420. However, it may be formed of a uniform diameter to match the inner diameter of expanding inner layer 420, or of a stepped diameter to match both the inner diameter of expanding inner layer 420 at its proximal and distal ends. After insertion of the adjustable sheath into the vessel, introducer device 510 is removed to allow other devices to be routed through the inner lumen of adjustable sheath 200.

Introducer device 510 may include a small hole at its tip to permit the passage of a wire previously inserted into the vessel.

Introducer device 510 may be constructed in multiple pieces, with its outer temporarily clamped between two or more pieces such that the user may adjust the position of the introducer pieces to release outer elastomeric tube 410. In an alternative embodiment, the outer elastomeric tube 410 may fold over within the expanding inner layer 420 at the distal end 240 and be retained by the introducer device 510 during vascular insertion and become released during removal of the introducer device 510, as described above.

Figures 6A, 6B:
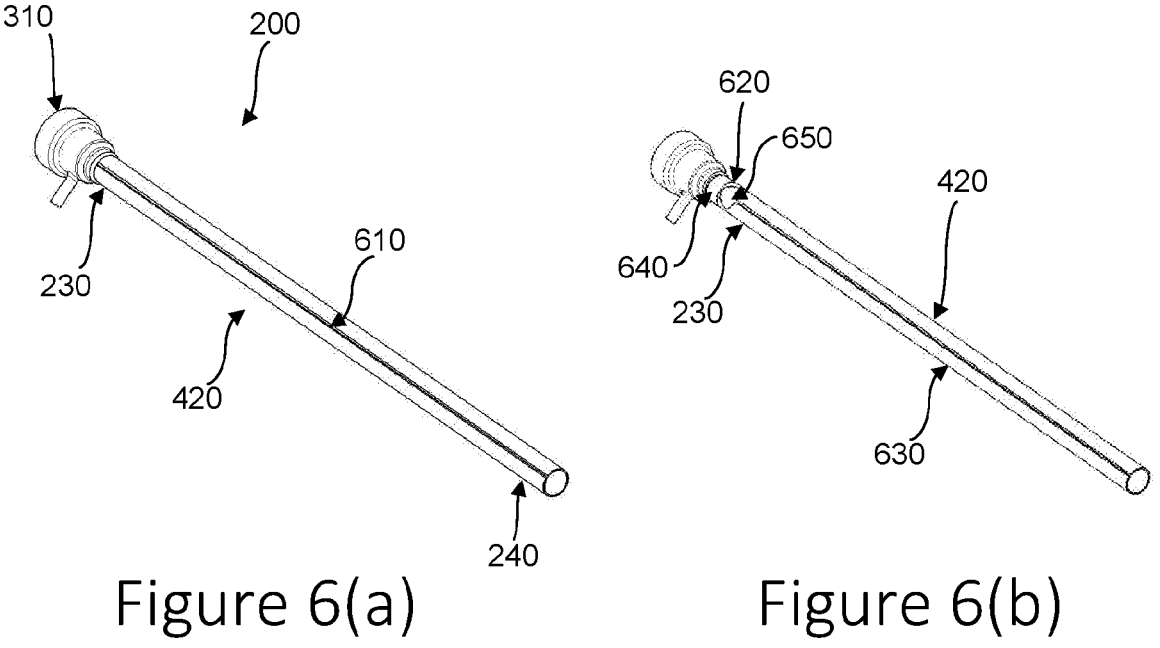
FIG. 6(a) illustrates a straight cut inner layer.
FIG. 6(b) illustrates a straight cut inner layer having a further cut-out portion, and FIG. 6(c) illustrated a spiral cut inner layer.
Figure 6C:
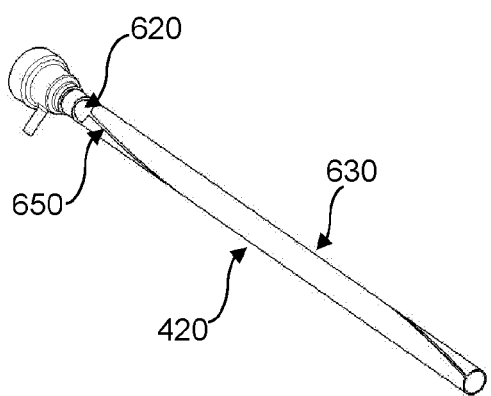

FIGS. 6(*a*) to 6(*c*) illustrate adjustable sheath 200 with outer elastomeric tube 410 removed. As shown in FIG. 6(*a*) expanding inner layer 420 is formed as a sheet cut such that, when coiled in a tapered overlapping arrangement, it has a single longitudinal join line 610. At proximal end 230, outer elastomeric tube 410 has a portion with no taper to promote a robust seal to the vascular opening. Non-tapered proximal end 230 is circumferentially continuous with the remaining portion of expanding inner layer 420 but shares a contiguous axial seam or joint line.

Expanding inner layer 420 may be cut and shaped into many different shapes. As an alternative, it may be cut so that, in its relaxed state, it is coiled to form a cylinder with no taper wherein the taper induced by a tapered outer tube.

FIGS. 6(*b*) and 6(*c*) illustrate an optional feature wherein the expanding inner layer 420 is further characterised by cut-out section 620, at distal end 240 of tapered section 630, separating tapered section 630 from non-tapered section 640. Cut-out section 620 forms an opening 650 in expanding inner layer 420, whereby the opening extends partially around the circumference of sleeve 220 to enable tapered section 630 to continue to non-tapered section 640 without causing the kinking and localised collapse of sleeve 220. Cut-out section 620 may also promote the ease of manufacture by reducing the risk of misfeeding of the inserted device between the expanding inner layer and the outer elastomeric tube. It may also improve the buckling and kinking strength of the adjustable sheath. The shape of the opening can be selected to be a variety of shapes, for example circular, triangular, ovoid, or T-shaped. The selected shape may be optimised by trial, error and testing of the desired physical properties of the adjustable sheath.

FIG. 6(*c*) illustrates an alternative embodiment wherein tapered section 630 is discontinuous. The discontinuous section is rectangular along the entire length of the tapered section 630, but the degree of overlap along the length of the tapered section increases from the proximal end to the distal end, creating helical edge 650 along the length of the tube.

Figure 7A:
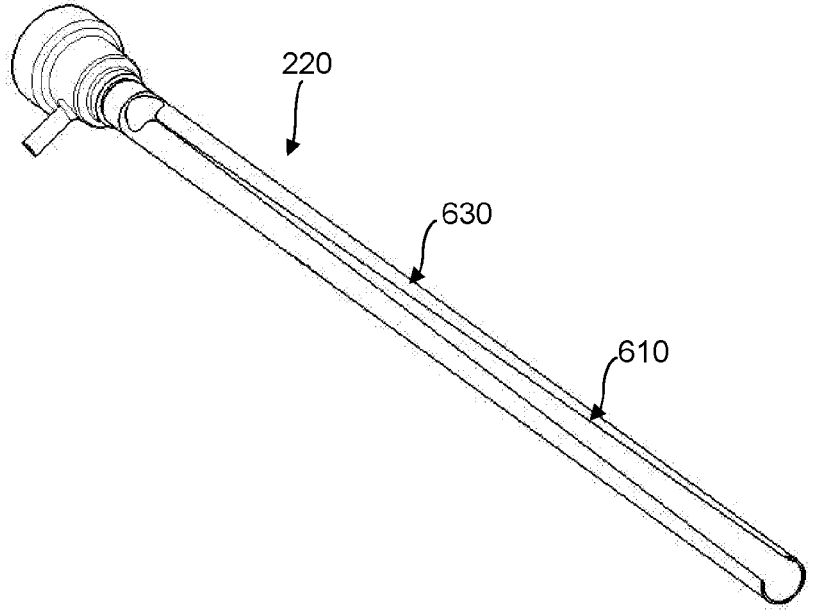
FIG. 7(a) provides a front perspective view of an adjustable sheath according to embodiments in an expanded form with the outer elastomeric tube removed and showing a v-cut inner layer, and FIG. 7(b) provides a side section view of the inner layer in an expanded, partially expanded and a retracted position.
Figure 7B:
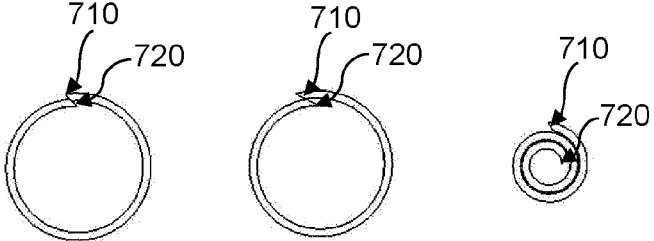

FIG. 7(*a*) illustrates an alternative embodiment wherein in the expanded state the edges are not parallel, or V-cut, where the circumference of the inner layer at the distal end is smaller than the circumference of the inner layer at the proximal end. This arrangement can promote a smaller overall distal diameter through a reduced material thickness due to the overlap in the layer, as illustrated in FIG. 7(*a*). When overexpanded, tapered section 630 will separate at join line 610. To prevent expanding inner layer 420 from locking in an expanded position within the vessel as a consequence of one blunt edge of expanding inner layer 420 becoming wedged upon the other blunt edges of expanding inner layer 420, the edges of the overlapping portions may be cut to be rounded or cut at a non-orthogonal angle. FIG. 7(*b*) illustrates the movement of one edge of expanding inner layer 420 against the other when being retracted following overextension, when cut at a non-orthogonal angle. When the edges abut one against the other, outer edge 710 slides over inner edge 710 until the expanding inner layer 420 is wound back to its approximate starting position.

In an alternative embodiment, the expanding inner layer 420 is created through a helically wound continuous strip or wire, characterised by a strip or wire thickness of dimension 'W', wound with a helical pitch of between 'W' and '2W'. The helical winding can be constructed of wire such as titanium, titanium alloy or stainless steel, or of a polymeric material such as polyester, polyethylene, polypropylene or other biocompatible material. The helical winding is tapered from distal end to a proximal end.

In a further alternative embodiment, the expanding inner layer 420 is formed by a continuous thin strip with a series of orthogonal wound coils propagating from one edge such that the coils wind back over the continuous strip. The wound coils are typically of length between 1 mm and 10 mm, with a spacing between them of 0.1 mm to 10 mm. In certain embodiments the diameter of each coil may be consistent along the length of the continuous strip, or varying diameter along the length whereby at least the coil at the distal end is a smaller diameter to the coil at the proximal end.

To permit the removal of air trapped between outer elastomeric tube 410 and expanding inner layer 420 prior to insertion of the adjustable sheath within the vascular system, certain embodiments may incorporate an opening in proximal end 230 of the outer elastomeric tube 410, which is closed with a valve (not shown). In use, prior to a medical procedure fluid such as saline or a sterilising agent may be introduced to the space between the inner and outer tubes through a valve.

To promote visibility of the adjustable sheath to x-ray imaging equipment during medical procedures, a radio opaque marker may be incorporated into the sleeve, in particular at the distal end 240. The marker may be a metallic wire such as nitinol bonded or stitched to the tube, or polymer-based such as a tungsten-filled nylon, polyethylene or polyurethane bonded to the tube, or similar components know to those skilled in the art. The radio opaque marker can be incorporated at one of any number of places in the expanding inner layer 420 or the outer elastomeric tube 410.

Preliminary Testing of Embodiments

Expansion and Retraction

Design: Measure the sheath diameter before insertion of the introducer within the sheath, and after retraction of the introducer. Report the percentage retraction of the sheath to its original diameter. Report the force required to retract the introducer.

Acceptance Criteria: Target maximum retraction percentage.

Sample Size Tested: One sample of a benchmark sheath, prototype sheath with straight cut taper, prototype sheath with spiral cut taper, prototype sheath with v-cut taper.

Methods: The proximal outer diameter and the distal end outer diameter of the test sheaths were measured before insertion of the introducer. The introducer was then inserted through the sheath, until it protruded through the distal end. Then the introducer was pulled back through the sheath and fully removed. The force to retract the introducer was recorded to assess any difficulty in retraction. The sheath distal end outer diameter was then remeasured to assess the amount of retraction or spring-back. The retractability percentage was then calculated as a percentage of the initial distal size reduction.

Results

| (mm) | Benchmark | Straight Cut | Spiral Cut | V cut |
|---|---|---|---|---|
| Initial Proximal Diameter | 7.1 | 7.1 | 7.1 | 7.1 |
| Initial Distal Diameter | 7.1 | 5.2 | 4.8 | 4.6 |
| Initial Distal size reduction | 0 | 1.9 | 2.3 | 2.5 |
| Force to retract | N/A | 17N | 16N | 15N |
| Final Diameter | 7.1 | 6.1 | 5.9 | 5.6 |
| Retractability % | 0% | 53% | 52% | 60% |

All samples experienced the smooth insertion of the introducer, with none requiring excessive force to insert the introducer. All adjustable sheaths demonstrated the characteristic of retracting to the limit of the sheath's capacity once the introducer had protruded past the end of the sheath.

After retraction of the introducer the V-cut prototype did not fully retract due to the cut edges colliding and failing to lap correctly. The outer layer of the V-cut prototype pulled back from the end of the inner layer by approximately 4 mm, possibly due to increased friction against the introducer.

Conclusion: All prototype sheaths demonstrated the ability to retract after insertion and removal of the introducer. The V-cut prototype gave the smallest distal end measurements but did not retract as intended. The straight cut and spiral cut prototypes showed nearly equivalent performance, however other performance characteristics should be considered when selecting a preferred design. The force required to retract the valve delivery system is not excessive for any of the designs, and would not pose a problem for a user, or a risk of damage.

Bendability

Design: Measure the force required to deflect the sheath without the introducer at angles of up to 30°.

Acceptance Criteria: Force the sheath to bend at an angle up to 30°. This should not exceed the benchmarked force.

Sample Size Tested: One sample of benchmark sheath, prototype sheath with straight cut taper, prototype sheath with spiral cut taper, prototype sheath with v-cut taper.

Method: A jig was constructed to hold the sheath, with a cantilever length of 200 mm. A hand-held force gauge was used to deflect the sheath and display the applied force in grams. The applied force was converted to N for consistency.

Results: The table below shows the force in N to deflect each sample.

| Angle (degrees) | Benchmark | Straight Cut | Spiral Cut | V cut |
|---|---|---|---|---|
| 0 | 0 | 0 | 0 | 0 |
| 10 | 0.44 | 0.29 | 0.34 | 0.20 |
| 20 | 0.59 | 0.39 | 0.59 | 0.39 |
| 30 | 0.78 | 0.44 | 0.59 | 0.49 |

Figure 8:
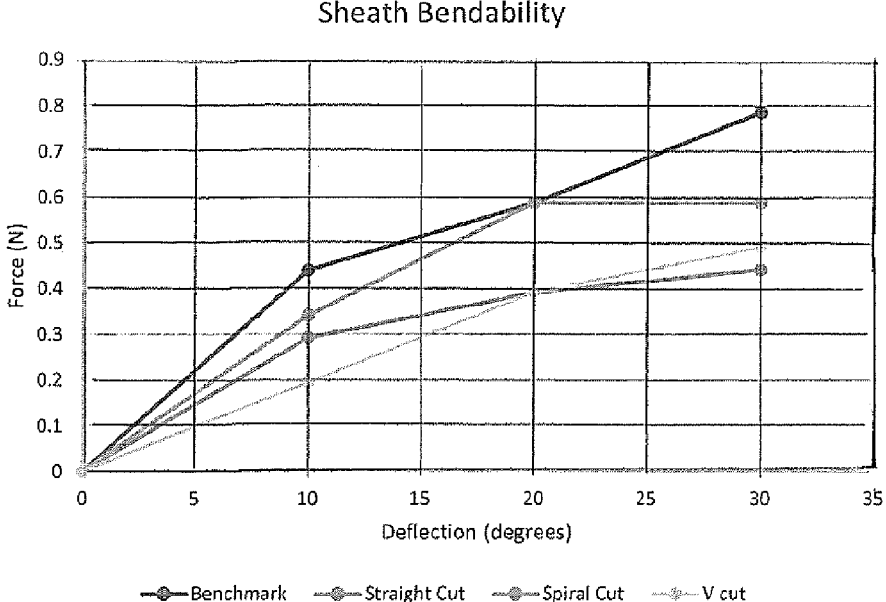
FIG. 8 provides a graphical representation of sheath bendability for adjustable sheaths according to embodiments having a straight cut, spiral cut and v-cut inner layer.

Conclusion: All prototype sheaths demonstrated improved bendability compared to the benchmark sample. The three different prototype sheaths displayed different bending and stiffness characteristics as demonstrate in FIG. 8.

Sheath Kinkability

Design: Measure the force required to kink the sheath, and the angle at which kinking occurs.

Acceptance Criteria: Angle required to kink the sheath should exceed the benchmark.

Sample Size Tested: One sample of the benchmark sheath, a prototype sheath with a straight cut taper, a prototype sheath with a spiral cut taper, a prototype sheath with a v-cut taper.

Method: A jig was constructed to hold the sheath, at a cantilever length of 200 mm. A hand-held force gauge was used to deflect the sheath and display the force applied in grams. Applied force was been converted to N for consistency. The angle to kink was read with reference to the template, which represents the angle between the sheath axis and a line from the point of bending to the sheath distal end.

Results:

| | Benchmark | Straight Cut | Spiral Cut | V cut |
|---|---|---|---|---|
| Force to kink (N) | 0.6867 | 0.981 | >1.4 | >1 |
| Angle to kink (deg) | 30 | 90 | >90 | >90 |

The spiral cut and v cut samples were able to bend beyond an angle of 90 degrees without kinking. The test for these samples was stopped at this point as the samples exceeded the testing capacity.

Conclusion: All prototype devices demonstrated improved resistance to kinking compared with the benchmark. The V-cut sample and spiral cut samples both deflected further than the straight cut sample without kinking.

Manufacture of Embodiments

The adjustable sheath is constructed by manufacturing the expanding inner layer and the outer elastomeric tube, assembling and bonding both components to a commercially available collar having a haemostatic valve.

The expanding inner layer is manufactured from medical grade polyamide according to standard extrusion or injection moulding techniques. For a straight cut inner layer, the raw material is extruded into a long tapered cylindrical shape and a slit cut along the length of the shape.

For a helical inner layer, once the inner layer is moulded to a desired size and shape, the layer is heat shrunk around a mould of the desired diameter to form a cylindrical portion to bond to the collar. The remaining sheet portion of the layer is cut at an oblique angle to a shape required to coil within the outer elastomeric tube.

The outer elastomeric tube is formed from silicone to a desired tapered shape using resin moulding techniques know to skilled persons to be suited for moulding and curing thin silicone sheets and tubular structures. The proximal section of the outer elastomeric tube is formed to the same or a slighter larger diameter of the cylindrical portion of the expanding inner layer.

The sheet portion of the expanding inner layer is manually coiled to a smaller diameter than the outer elastomeric tube and placed within the tube once aligned at the proximal end. A small amount of adhesive is applied at the proximal (or wider) edge of the tapered sleeve such that the adhesive is in contact with the outer elastomeric tube and the expanding inner layer. The proximal edge is then placed around the opening of a commercially available haemostatic valve to bind both the expanding inner layer and the outer elastomeric tube to the collar of the haemostatic valve. Once the adhesive has been allowed to set the sheath is ready for use.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

It will be understood that the terms 'fastener' or 'fastening', 'coupling' or 'sealing' when used alone or together with other terms such as 'means' or others, may be used interchangeably where interpretation of the term would be deemed by persons skilled in the art to be functionally interchangeable with another. Further, the use of one of the aforementioned terms does not preclude an interpretation when another term is included.

The various apparatuses and components of the apparatuses, as described herein, may be provided in various sizes and/or dimensions, as desired. Suitable sizes and/or dimensions will vary depending on the specifications of connecting components or the field of use, which may be selected by persons skilled in the art.

It will be appreciated that features, elements and/or characteristics described with respect to one embodiment of the disclosure may be used with other embodiments of the invention, as desired.

Although the preferred embodiments of the present disclosure have been disclosed for illustrative purposes, those skilled in the art will appreciate that various modifications, additions and substitutions are possible, without departing from the scope and spirit of the disclosure and accompanying claims.

It will be understood that when an element or layer is referred to as being "on" or "within" another element or layer, the element or layer can be directly on or within another element or layer or intervening elements or layers. In contrast, when an element is referred to as being "directly on" or "directly within" another element or layer, there are no intervening elements or layers present.

As used herein, the term "and/or" includes any and all combinations of one or more of the associated listed items.

It will be understood that, although the terms first, second, third, etcetera, may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section could be termed a second element, component, region, layer or section without departing from the teachings of the present disclosure.

Spatially relative terms, such as "lower", "upper", "top", "bottom", "left", "right" and the like, may be used herein for ease of description to describe the relationship of one element or feature to another element(s) or feature(s) as illustrated in the figures. It will be understood that spatially relative terms are intended to encompass different orientations of structures in use or operation, in addition to the orientation depicted in the drawing figures. For example, if a device in the drawing figures is turned over, elements described as "lower" relative to other elements or features would then be oriented "upper" relative the other elements or features. Thus, the exemplary term "lower" can encompass both an orientation of above and below. The device may be otherwise oriented (rotated 90 degrees or at other orientations) and the spatially relative descriptors used herein should be interpreted accordingly.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "including," "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Embodiments of the description are described herein with reference to diagrams and/or cross-section illustrations, for example, that are schematic illustrations of preferred embodiments (and intermediate structures) of the description. As such, variations from the shapes of the illustrations as a result, for example, of manufacturing techniques and/or tolerances, are to be expected. Thus, embodiments of the description should not be construed as limited to the particular shapes of components illustrated herein but are to include deviations in shapes that result, for example, from manufacturing.

Unless otherwise defined, all terms (including technical and scientific terms) used herein have the same meaning as commonly understood by one of ordinary skill in the art to which this description belongs. It will be further understood that terms, such as those defined in commonly used dictionaries, should be interpreted as having a meaning that is consistent with their meaning in the context of the relevant art and will not be interpreted in an idealised or overly formal sense unless expressly so defined herein.

Any reference in this specification to "one embodiment," "an embodiment," "example embodiment," etc., means that a particular feature, structure, or characteristic described in connection with the embodiment is included in at least one embodiment of the description. The appearances of such phrases in various places in the specification are not necessarily all referring to the same embodiment. Further, when a particular feature, structure, or characteristic is described in connection with any embodiment, it is within the purview of one skilled in the art to effect and/or use such feature, structure, or characteristic in connection with other ones of the embodiments.

Embodiments are also intended to include or otherwise cover methods of using and methods of manufacturing any or all of the elements disclosed above.

While the invention has been described above in terms of specific embodiments, it is to be understood that the invention is not limited to these disclosed embodiments. Upon reading the teachings of this disclosure many modifications and other embodiments of the invention will come to the mind of those skilled in the art to which this invention pertains, and which are intended to be and are covered by both this disclosure and the appended claims.

All publications mentioned in this specification are herein incorporated by reference. Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia or elsewhere before the priority date of each claim of this application.

It is indeed intended that the scope of the invention should be determined by proper interpretation and construction of the appended claims and their legal equivalents, as understood by those skilled in the art relying upon the disclosure in this specification and the attached drawings.

The invention claimed is:

1. A retractable sheath for protecting a luminal surface of a blood vessel from the introduction of a medical device within the blood vessel, the retractable sheath comprising:
   a rigid collar having an inner surface defining an opening extending through the collar, the rigid collar having attached thereto a retractable elongated sleeve having a proximal opening and a distal opening defining a luminal channel therebetween, the retractable elongated sleeve comprising two separate layers including a continuous elastomeric outer layer and an expandable inner layer discontinuous at least in part,
   a discontinuous part of the expandable inner layer comprising a stiff polymeric sheet characterized as having outward annular resistance when forcibly coiled, the stiff polymeric sheet forming at least part of the expandable inner layer when coiled and positioned longitudinally within a lumen formed by the continuous elastomeric outer layer and positioned substantially in contact with a luminal surface of the continuous elastomeric outer layer, wherein the rigid collar is attached to the retractable elongated sleeve at the proximal opening of the retractable elongated sleeve, and wherein the expandable inner layer comprises a substantially cylindrical continuous portion terminating at the proximal opening and a discontinuous stiff polymeric sheet portion terminating at the distal opening when coiled and positioned longitudinally within the lumen formed by the continuous elastomeric outer layer and positioned substantially in contact with the luminal surface of the continuous elastomeric outer layer.

2. The retractable sheath according to claim 1, wherein the discontinuous stiff polymeric sheet portion is configured to coil in an overlapping arrangement in its relaxed state and to coil helically about the longitudinal axis of the retractable elongated sleeve.

3. The retractable sheath according to claim 2, wherein an edge of the discontinuous stiff polymeric sheet portion winds helically about the longitudinal axis of the retractable elongated sleeve.

4. The retractable sheath according to claim 3, wherein the discontinuous stiff polymeric sheet portion is wound about the longitudinal axis of the sheath a number of times approximately equal to the number of times the distal portion is wound plus about 0.5 to about 1.5.

5. The retractable sheath according to claim 1, wherein the stiff polymeric sheet comprises at least three edges, wherein at least one edge terminates in an oblique cut.

6. The retractable sheath according to claim 5, wherein at least two substantially opposite edges of the at least three edges intersect at a point or edge defining the distal opening and at least one of the at least two substantially opposite edges are formed by an oblique cut.

7. A retractable sheath according to claim 1, wherein the retractable elongated sleeve is longitudinally tapered at least partially between the proximal opening and the distal opening.

8. A retractable sheath according to claim 7, wherein a distal sleeve edge defining the distal opening has a circumference at least about 20% smaller than a proximal sleeve edge defining a proximal circumference of the proximal opening.

9. A retractable sheath according to claim 8, wherein the distal sleeve edge defining the distal opening has a circumference at least about 25% smaller than the proximal sleeve edge defining the proximal circumference of the proximal opening.

10. A retractable sheath according to claim 1, wherein the stiff polymeric sheet is formed from a material comprising at least one member selected from the group consisting of polyethylene, polypropylene, nylon, polyester, PTFE, copolymers thereof or another biologically compatible polymer.

11. A retractable sheath according to claim 1, wherein the continuous elastomeric outer layer is comprised of an elastomeric material, the continuous elastomeric outer layer capable of being expanded upon stretching of the elastomeric material and retracted upon relaxation of the elastomeric material, and wherein the elastomeric material is capable of returning to a circumference of about 135% or less of its initial circumference once retracted.

12. A retractable sheath according to claim 11, wherein the continuous elastomeric outer layer capable of being expanded upon stretching of the elastomeric material to about 1.35 times or greater of its unstretched circumference.

13. A retractable sheath according to claim 12, wherein the continuous elastomeric outer layer comprises a thickness of about 0.1 mm.

14. A retractable sheath according to claim 1, wherein the continuous elastomeric outer layer is formed from a silicone material or a silicone composite material, and comprises a thickness of about 0.2 mm or less.

15. A retractable sheath according to claim 1, comprising a rigid introducer within the luminal channel of the retractable elongated sleeve and protruding past the distal end of the retractable elongated sleeve.

16. A retractable sheath according to claim 1, wherein the retractable elongated sleeve comprises a radio opaque marker.

17. A method of use of the retractable sheath according to claim 1 comprising the steps of: obtaining the retractable sheath, passing a rigid introducer through the luminal channel of the retractable sheath, and introducing the retractable sheath into a blood vessel.

18. A method of manufacture of the retractable sheath according to claim 1 comprising the steps of: obtaining the rigid collar, the continuous elastomeric outer layer and the expandable inner layer, attaching the expandable inner layer at the proximal opening with the rigid collar, and placing the expandable inner layer within the continuous elastomeric outer layer.

19. A retractable sheath, for protecting a luminal surface of a blood vessel from the introduction of a medical device within the blood vessel, the retractable sheath comprising:

a rigid collar having an inner surface defining an opening extending through the collar, the rigid collar having attached thereto a retractable elongated sleeve having a proximal opening and a distal opening defining a luminal channel therebetween, the retractable elongated sleeve comprising two separate layers including a continuous elastomeric outer layer and an expandable inner layer discontinuous at least in part, a discontinuous part of the expandable inner layer comprising a stiff polymeric sheet characterized as having outward annular resistance when forcibly coiled, the stiff polymeric sheet forming at least part of the expandable inner layer when coiled and positioned longitudinally within a lumen formed by the continuous elastomeric outer layer and positioned substantially in contact with a luminal surface of the continuous elastomeric outer layer, wherein the rigid collar is attached to the retractable elongated sleeve at the proximal opening of the retractable elongated sleeve, wherein the continuous elastomeric outer layer and the expandable inner layer are movable with respect to one another, and a luminal surface of the continuous elastomeric outer layer and an outer surface of the expandable inner layer are movable against each other, wherein the retractable elongated sleeve comprises a lubricious layer or surface treatment between the luminal surface of the continuous elastomeric outer layer and the outer surface of the expandable inner layer comprising at least one member selected from the group consisting of silicone, glycerine oil, PTFE, or a hydrophilic polymer to reduce the coefficient of friction, and wherein the expandable inner layer is integrally formed from a substantially uniform stiff polymeric material comprising a notch or cut-out between the substantially cylindrical continuous portion and the discontinuous stiff polymeric sheet portion.

* * * * *